United States Patent [19]

Zhau et al.

[11] Patent Number: 5,221,612

[45] Date of Patent: Jun. 22, 1993

[54] UNIQUE PROTEIN MARKER FOR BLADDER CANCER

[75] Inventors: Haiyen E. Zhau; Richard J. Babaian, both of Houston, Tex.

[73] Assignee: Board of Regents, The University of Texas System, Austin, Tex.

[21] Appl. No.: 318,790

[22] Filed: Mar. 3, 1989

[51] Int. Cl.⁵ .......................................... G01N 33/538
[52] U.S. Cl. ................................. 435/7.92; 435/7.1; 436/536; 436/516; 436/174; 436/177; 436/178; 436/813; 436/828; 436/825
[58] Field of Search .......................... 435/7, 7.1, 7.92; 436/516, 526, 813, 174, 177, 178; 825/813, 828

[56] References Cited

FOREIGN PATENT DOCUMENTS

2140030 11/1984 United Kingdom .
90/00222 5/1990 World Int. Prop. O. .

OTHER PUBLICATIONS

Paulie, S. et al. Monoclonal Antibodies to Antigens Associated with Transitional Cell Carcinoma of the Human Urinary Bladder, Cancer Immunol. Immunother. 17:173, 1984.
Gozzo et al.: Use of Heterogeneous & Monospecific Antisera for the Diagnosis of Bladder Cancer, J. Urol. 118:748 1977.
Hagashi, G. et al., Preliminary Identification of a Tumor-Associated Glycoprotein and Bilharzial Bladder Cancer Urine. Int. J. Cancer, 32:445, 1983.
De Fazio, S. R. et al., Tumor-Associated Antigens in the Urine of Patients with Bladder Cancer. Cancer Res. 42:2913, 1982.
Braesch-Anderson, S. et al., Isolation and Characterization of Two Bladder Carcinoma-Associated Antigens. J. Immunol. Method., 94:145, 1986.
Koho, H. et al., Monoclonal Antibodies to Antigens Associated with Transitional Cell Carcinoma of the Human Urinary Bladder. Cancer Immunol. Immunother., 17:165, 1984.
Babaian, R. J. et al., Immune Complexes in Urine and Serum of Patients with Bladder Cancer. J. Urol., 131:463, 1984.
Hellstrom, I. et al., Monoclonal Antibodies to Cell Surface Antigens Shared by Chemically Induced Mouse Bladder Carcinomas. Chem. Abstr., 102:462, 1985.
Lee. V. K. et al., Monoclonal Antiidiotypic Antibodies Related to a Murine Oncofetal Bladder Tumor Antigen Induce Specific Cell-Mediated Tumor Immunity. Prac. Natl. N. Acad. Sci., 82:6286, 1985.

(List continued on next page.)

*Primary Examiner*—Christine Nucker
*Assistant Examiner*—Jeffrey Stucker
*Attorney, Agent, or Firm*—Arnold, White & Durkee

[57] ABSTRACT

The present invention involves a method for detecting bladder cancer in a subject. The method preferably comprises first collecting a urine sample from the subject. The presence of a proteinaceous substance having a molecular weight of about 180 kDa according to its relative electrophoretic migration rate through detergent-containing polyacrylamide gel is then measured. This substance reversibly binds concanavalin A and is complexed with gamma globulin while in the urine. The gamma globulin complex binds to Staphlococcal protein A. Said proteinaceous substance, when present in detectable amount, is an indicator of bladder cancer.

The method of the present invention for diagnosing bladder cancer in a subject may also be described as comprising detection in a urine sample from said subject of a proteinaceous substance having a molecular weight of about 180 kDa and being unreactive with antibodies specifically binding to carcinoembryonic antigen or epidermal growth factor receptor. When an antibody is used for the present method of diagnosis, an initial step for preparing an antibody specifically binding a urinary 180 kDa antigen present in urine of bladder cancer victims is carried out. This antibody of course may be prepared by others and merely obtained by commercial purchase. In any case said antibody may be used to detect the bladder cancer-specific 180 kDa antigen of the present invention in patient urine. This antibody is most preferably monoclonal or may be polyclonal.

7 Claims, 7 Drawing Sheets

OTHER PUBLICATIONS

Zhau, H. et al., Detection of Immunoglobulin Reactivity in Urine Specimens of Bladder Cancer Patients. J. Urol., 139:241a, 1988.

Johansson, B. et al., Proteinuria in patients with urinary tract tumors. Scand. J. Urol. Nephrol., 5:229, 1971.

Hakala, T. R., et al., Humoral cytotoxicity in human transitional cell carcinoma. J. Urol., 111:382, 1974.

Troye, M., et al., The use of Fab fragments of anti-human immunoglobulin as analytic tools for establishing the involvement of immunoglobulin in the spontaneous cytotoxicity to cultured tumor cells by lymphocytes from patients with bladder carcinoma and from healthy donors. J. Immunol., 119:1061, 1977.

O'Brien, P., et al. Qualitative analysis of proteinuria associated with bladder cancer. Invest. Urol., 17:28, 1979.

Wahren, B. et al. Tumor markers in gastrointestinal and urothelial cancers. Applied Methods in ONcology, 2:338, 1979.

Betkerur, V. et al. Screening tests for detection of bladder cancer. Urology, 16:16, 1980.

Betkerur, V. et al. Urinary immunoglobulin A in the diagnosis of bladder cancer. J. Surg. Oncol., 16:215, 1981.

Huland, H., et al. The value of urinary cytology, serum and urinary carcinoembryogenic antigen, rheumatoid factors, and urinary immunoglobulin concentration as tumor markers or prognostic factors in predicting progression of superficial bladder cancer.

Langone, J. J. et al. Applications of immobilized protein A in immunochemical techniques. J. Immunol. Methods, 55:277, 1982.

Laemmli, U. K. et al. Cleavage of structural proteins during the assembly of the head of bacteriophage T4. Nature, 227:680, 1970.

Lowry, O. H. et al. Protein measurement with the folin phenol reagent. J. Biol. Chem., 193:265, 1951.

Towbin, H. et al. Immunoblotting and dot immunobinding: current status and outlook. J. Immunol. Methods, 72:313, 1984.

Ey, P. L. et al. Isolation of pure IgG, IgG2a and IgG2b immunoglobulins from mouse serum using protein A-SEPHAROSE. Immunochemistry, 15:429, 1978.

Kobayashi, K., et al. Circulating immune complexes in patients with bladder cancer and other malignancies of the urogenital tract. Urol. Int., 39:232, 1984.

Hemmingsen, L., et al. Urinary protein profiles in patients with urothelial bladder tumors. Br. J. Urol., 53:324, 1981.

Mayes, E. LO. V., et al. Biosynthesis of the epidermal growth factor receptor in A431 cells. EMBO, 3:531, 1984.

Gozzo, J. J., et al. Detection of tumor-associated antigens in urine from patients with bladder cancer. J. Urol., 124:804, 1980.

Rote, N. S., et al. Tumor associated antigens detected by autologous sera in urine of patients with solid neoplasms. J. Surg. Res., 29:18, 1980.

Rife, C. C., et al. Urine cytology of transitional cell neoplasms. Urol. Clin. North Am., 6:599, 1979.

Matthews, D. E. et al. Using and Understanding Medical Statistics. Basel, New York: Karger, pp. 20–26, 1985.

Johansson, B. et al. Proteinuria in patients with uroepithelial tumors with special regard to tumor size, clinical staging and grade of malignancy. Scand. J. Urol. Nephrol., 9:52, 1974.

Chao, H. E. et al. Neonatal Imprinting and Hepatic Cytochrome, p. 450, Molecular Pharmacology 21:744, 1982.

Kohler, G., and Milstein, C. Nature (Lond.) 256:495, 1975.

Chan, J. C., Keck, M. E., and Li, W. J. Biochem. Biophys. Res. Comm. 134:1223, 1986.

Hsu, S. M., Raine, L., and Fanger, H. Am. J. Clin. Pathol. 75:734, 1981.

UNIQUE PROTEIN MARKER FOR BLADDER CANCER

BACKGROUND OF THE INVENTION

The present invention involves the diagnosis of bladder cancer comprising detection of a particular and unique proteinaceous urine component.

Bladder cancer consists of a heterogenous group of tumors with varied capacities for invasion and metastasis. This disease accounts for 2 percent of all malignancies and is the 5th most prevalent cancer among adults in the United States.[1] In the effort to identify biochemical markers that may have diagnostic and prognostic value, various noninvasive tests have been developed, including tests to identify tumor-associated markers in the urine, serum, and bladder cancer tissue specimens. Among the various tumor-associated markers studied, urinary immunoglobulins have been found to increase in persons who have bladder cancer[2-7] and appear to have some diagnostic and prognostic value.[8-10] There are no data, however, to indicate that these antibodies are specifically directed toward bladder carcinoma antigens.

In an earlier communication[11] the present inventors demonstrated that, in comparison to normal controls, the immunoglobulin G heavy- and light-chain fractions appear to be enriched in the urine samples of persons with bladder cancer. The urine of patients with bladder cancer has long been subject to scrutiny as a possible source of either a diagnostic or a prognostic tumor marker. Since urine comes in direct contact with and bathes bladder neoplasms and is known to contain immunoglobulins,[2,6] antigens,[22,23] exfoliated tumor cells,[24] and other proteins,[6,10] it continues to be the medium of greatest interest in the search for a common tumor-associated protein. Although one of the present inventors has previously reported on the apparent relationship of urinary immune complexes to the stage of disease, no specific bladder cancer-associated antigen in immune complex has been identified.[18]

SUMMARY OF THE INVENTION

The present invention involves a method for detecting bladder cancer in a subject. The method preferably comprises first collecting a urine sample from the subject. The presence of a proteinaceous substance having a molecular weight of about 180 kDa according to its relative electrophoretic migration rate through detergent-containing polyacrylamide gel is then measured. This substance reversibly binds concanavalin A and is complexed with gamma globulin while in the urine. The gamma globulin complex binds to Staphlococcal protein A. Said proteinaceous substance, when present in detectable amount, is an indicator of bladder cancer.

The unique proteinaceous substance of the present invention is immunochemically non-reactive with antibodies directed toward carcinoembryonic antigen or epidermal growth factor receptor, other potential urinary proteins having molecular weights of about 180 kDa. This proteinaceous substance may also be measured through use of an antibody specifically binding to said proteinaceous substance by any of the immunochemical methods well known to those skilled in the relevant arts.

The present method for diagnosing bladder cancer in a subject may also involve initially detecting in a urine sample from said subject a proteinaceous substance having a molecular weight of about 180 kDa according to its relative electrophoretic migration rate through detergent-containing polyacrylamide gel, the substance being defined as reversibly binding to concanavalin A and as being in a complex with gamma globulin in the urine. Said complex binds to Staphlococcal protein A.

The method of the present invention for diagnosing bladder cancer in a subject may also be described as comprising detection in a urine sample from said subject of a proteinaceous substance having a molecular weight of about 180 kDa and being unreactive with antibodies specifically binding to carcinoembryonic antigen or epidermal growth factor receptor. When an antibody is used for the present method of diagnosis, an initial step for preparing an antibody specifically binding a urinary 180 kDa antigen present in urine of bladder cancer victims is carried out. This antibody of course may be prepared by others and merely obtained by commercial purchase. In any case said antibody may be used to detect the bladder cancer-specific 180 kDa antigen of the present invention in patient urine. This antibody is most preferably monoclonal or may be polyclonal.

In greater detail, the present invention involves a more specific method for detecting bladder cancer in a subject. This more detailed method comprises: collecting a urine sample from the subject; filtering said urine sample to remove particulate matter; dialyzing said filtered sample to remove low molecular weight soluble substances; incubating the dialyzed, filtered sample with solid matrix-affixed protein A; separating the solid matrix-affixed protein A with material absorbed thereto; eluting absorbed material from the solid matrix-affixed protein A; separating proteinaceous components of the eluted material according to their molecular weights and charges; and identifying the presence and amount of proteinaceous substance having a molecular weight of about 180 kDa, said proteinaceous substance being indicative of bladder cancer.

DETAILED DESCRIPTION OF THE PREFERRED EMBODIMENT

Figure 1:
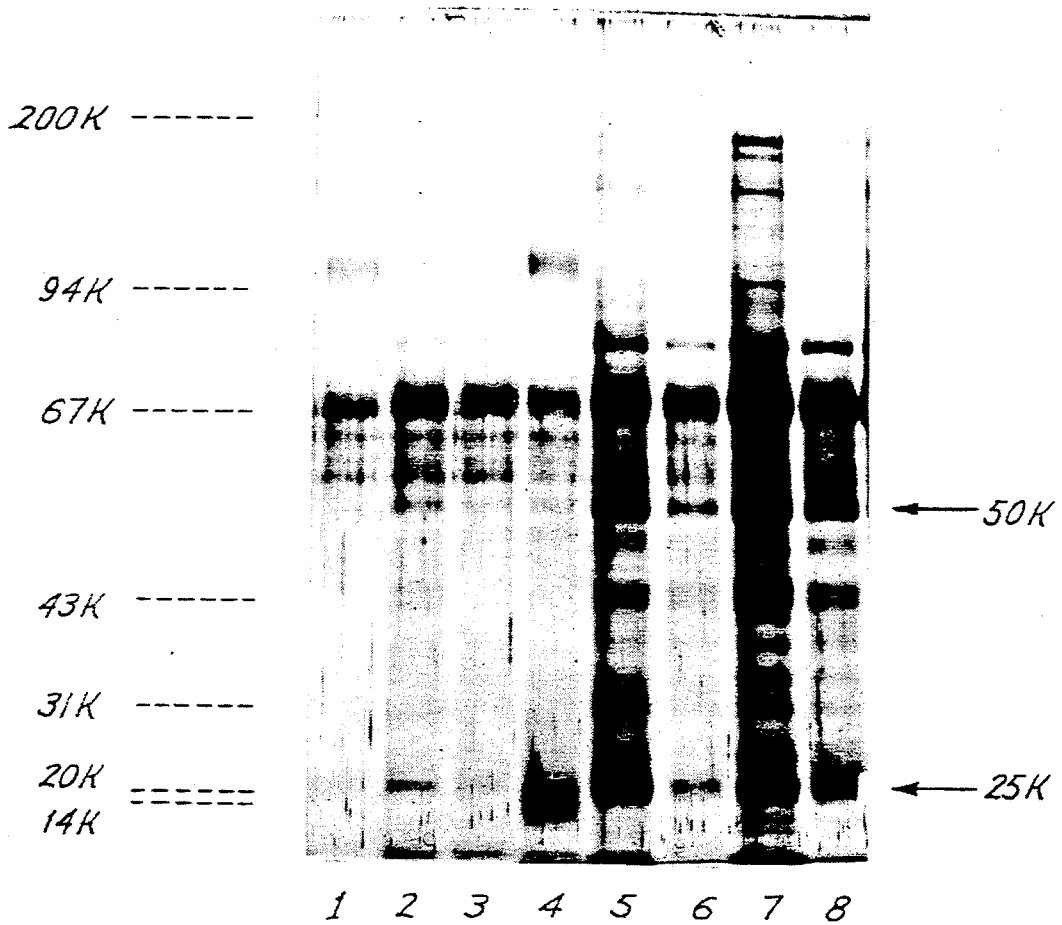
FIG. 1 shows profiles of silver-stained urine proteins obtained from normal controls (tracks 1 to 4) and bladder cancer patients (tracks 5 to 8) as analyzed by SDS-PAGE.

A new urine marker protein of 180 kDa that appears to be bladder cancer specific has been identified. This protein behaves like a glycoprotein but is immunochemically neither CEA nor EGFR. This protein is most likely derived from the cancer cells and may represent an antigen common to the urine of patients with bladder tumors. While the 180 kDa molecular weight is used herein, it is understood that it is approximate and may mean from 170 kDa to 190 kDa.

This protein was found to be present in a large number of patients who have bladder cancer, in particular those with transitional cell carcinoma of the bladder. The 180 kDa protein was absent from persons with other forms of neoplastic diseases and was not associated with bladder infection. A monoclonal antibody against the 180 kDa protein and use of such an antibody to measure this marker protein and to correlate its appearance with various stages and grades of bladder cancer are currently under development.

Urine samples from 93 patients who were scheduled to undergo radical cystectomy for transitional cell carcinoma of the bladder were examined for a common urinary tumor-associated marker protein. A 180-kDa marker was found in a large majority of the patients surveyed. No specimen from normal controls or from patients with other types of malignancy was found to contain this urinary protein. Thirteen clinicopathologic features of the bladder cancer patients were analyzed to determine whether any parameter could explain why some of the patients were marker negative. The only statistically significant finding was that a higher proportion of marker-negative patients than of marker-positive patients had received prior systemic chemotherapy (P=0.018). Consequently, this marker appeared to be highly specific for bladder cancer and to have considerable potential in diagnosing, staging, and monitoring the therapeutic responses of this malignancy.

These examples are presented to describe preferred embodiments and utilities of the present invention and are not meant to limit the present invention unless otherwise stated in the claims appended hereto.

EXAMPLE 1

The presence of tumor-related proteins in the urine specimens of 101 bladder cancer patients was studied, seeking a possible marker enabling diagnosis and prognosis of this disease. A marker protein of 180 kDa (as determined by sodium dodecyl sulfate polyacrylamide gel electrophoresis) was identified that was adsorbed by protein A conjugated to SEPHAROSE beads. This protein appeared to be a glycoprotein binding to concanavalin A-conjugated SEPHAROSE and elutable by alpha-methyl D-mannoside. It did not react immunochemically with antibodies prepared against carcinoembryonic antigen and epidermal growth factor receptor, both of which have an apparent MW close to 180 kDa (kilodalton).

This 180-kDa protein appeared in the urine of a majority of patients with transitional cell carcinoma but was absent from urine specimens of age-matched controls and of patients with benign prostatic hyperplasia or nine other cancers. The appearance of this 180-kDa protein was not associated with bladder infection or blood contamination, and occurred equally in men and women. This marker protein was detected with carcinoma in situ and with superficial and infiltrating bladder cancer at an overall incidence of 71.3 percent.

To investigate proteins that may be associated with bladder cancer, the present inventors searched and found applicable a method that has been previously used to detect immunoglobulins and antigen-antibody complexes in a number of diseases including cancer.[12] An important principle of this procedure is the adsorption of immunoglobulin and its associated protein(s) by protein A-SEPHAROSE beads. The adsorbed proteins were then dissociated from the affixed protein A, subjected to sodium dodecyl sulfate polyacrylamide gel electrophoresis (SDS-PAGE) and stained with silver for visualization. The present Example describes the discovery, detection and characterization of a 180-kDa protein that appears associated with immunoglobulins in the urine specimens obtained from patients with bladder cancer. This marker protein appeared to be glycosylated, contain an alpha-D-mannose moiety and may represent a tumor-associated antigen complexed with urinary immunoglobulins.

SAMPLE COLLECTION AND PROCESSING

Urine samples (80-100 ml) were collected from 101 patients about to undergo radical cystectomy for bladder cancer. Of these, 93 patients had transitional cell carcinoma, 4 had squamous cell carcinoma, 2 had sarcoma, and 1 each had adenocarcinoma or small cell carcinoma. Twenty-four of the patients from whom samples were collected had received chemotherapy and 6 had received radiation therapy (2 of the 6 received both irradiation and chemotherapy) within 1 year before cystectomy. The average age of patients was 65 years (range 27-82 years).

Control samples were obtained from 37 healthy individuals (24 aged 24–46 years and 13 aged 57–78 years) and from 35 patients with other forms of neoplastic diseases (cancers of the prostate, colon, cervix, vagina, ovary, liver, lung, esophagus, and pancreas). For comparative studies, serum specimens were also obtained from some of the patients with bladder cancer. In addition, in selected cases, urine specimens were collected postcystectomy either by catheter or from the ileal conduit to determine the source of this marker protein.

After collection, urine samples were transported immediately on ice to the research laboratory. The samples were filtered through a 0.2-micron membrane (Gelman Sciences, Ann Arbor, Mich.) to remove cell debris and possible bacterial contamination. The filtered samples then underwent a 48-hr dialysis against 4 changes of 4 liters of double-glass distilled water at 4° C. and were lyophilized and resuspended in the appropriate volume to give a 20-fold concentration. Samples were kept at −20° C. for short-term and −80° C. for long-term storage. The presence of urine sample bacterial infection was confirmed by a positive bacterial culture.

SDS-PAGE analysis

To obtain a total protein profile, 8-ug (microgram) protein samples were subjected to 7.5 percent (w/v) SDS-PAGE (sodium dodecyl sulfate-polyacrylamide gel electrophoresis) analysis according to the procedures of Laemmli.[13] This procedure alone, in most cases, failed to detect the presence of a 180-kDa marker protein. However, as described herein, subjecting the samples to protein A-SEPHAROSE treatment before SDS-PAGE analysis allowed clear identification of this marker protein.

To detect the 180-kDa protein, 1 mg total urinary protein was incubated with a 2.5-mg pre-soaked and washed staphylococcal protein A-SEPHAROSE beads (Sigma Chemical Co., St. Louis, MO) in 150 ul (microliter) phosphate-buffered saline (PBS) for 1.5 hour at 4° C. The protein A-SEPHAROSE-adsorbed fraction was collected after centrifugation. The pellet was washed 3 times with PBS, and the protein A-adsorbed proteins were then eluted with 50 ul SDS-PAGE sample buffer (10% [w/v]glycerol, 5% [v/v]2-mercaptoethanol, 2.3% SDS [w/v], 62.5 mM tris buffer, pH 6.80). The eluate was subjected to 7.5 percent SDS-PAGE analysis. The molecular weight (MW) of the protein was identified by a standard procedure employing the following protein markers as reference standards: phosphorylase b (94,000 MW), bovine serum albumin (68,000 MW), ovalbumin (43,000 MW), carbonic anhydrase (31,000 MW), soybean trypsin inhibitor (20,100 MW) and alpha-lactalbumin (14,400 MW) (Pharmacia LKB Biotechnology Inc., Piscataway, N.J.). Carcinoembryonic antigen (CEA) (200,000 MW) (CalBiochem, La Jolla, Calif.) was added to the above protein mixture as a high-molecular-weight standard. A known 180-kDa marker protein in positive urine samples was always included as a parallel internal marker. The gels were fixed and silver stained according to the procedure of Sammons et al.[14] Protein concentration was determined by the Lowry method[15] using bovine serum albumin as reference standard.

Detection of CEA and epidermal growth factor receptor (EGFR) by western blotting technique Two hundred and fifty micrograms of urine or serum proteins were analyzed by SDS-PAGE according to the procedures described above. The proteins were transferred electrophoretically to nitrocellulose paper and blotted with monoclonal antibodies specifically binding either CEA or EGFR (ICN ImmunoBiologicals, Lisle, Ill.) according to a western blot procedure described by Towbin et al.[16] For the detection of CEA, [$^{125}$I]-labeled CEA antibody ($2 \times 10^6$ cpm (counts per minute) per lane) was used, and the location of CEA was confirmed by the use of purified CEA (CalBiochem, La Jolla, Calif., 1.5 ug) as a reference standard. For the detection of EGFR, an avidin biotin-alkaline phosphatase detection system (Vector Laboratories Inc., Burlingame, Calif.) was used, and the presence of EGFR was confirmed by the use of A-431 cells, which contain abundant EGFR, as the reference cell line. Both EGFR and CEA were known to contain a single polypeptide with a MW in the range of 175–200 kDa.

Reactivity with concanavalin-conjuqated SEPHAROSE beads.

Urine protein (20 mg) was loaded on a concanavalin A(con-A)-SEPHAROSE column (1.5×15 cm). The column was washed with 0.1M phosphate buffer (pH 7.20) followed by 0.5M NaCl. The con A-bound protein was eluted by a 0 to 1.0M alpha-methyl-D-mannopyranoside continuous gradient and collected as 0.7-ml fractions. Ten micrograms of protein from each fraction was analyzed by SDS-PAGE.

Results of the above manipulations applied to bladder cancer diagnosis were as follows. Typical silver-stained SDS-PAGE protein profiles of urine specimens obtained from controls (tracks 1 to 4) and bladder cancer patients (tracks 5 to 8) are shown in FIG. 1. Silver-stained protein bands were more intense for urine samples obtained from bladder cancer patients than from controls. Proteins banded at immunoglobulin G heavy- and light-chain regions (arrows at 50- and 25-kDa regions) and at higher MW regions were also more intense in samples from bladder cancer patients than in those from controls.

Figure 2:
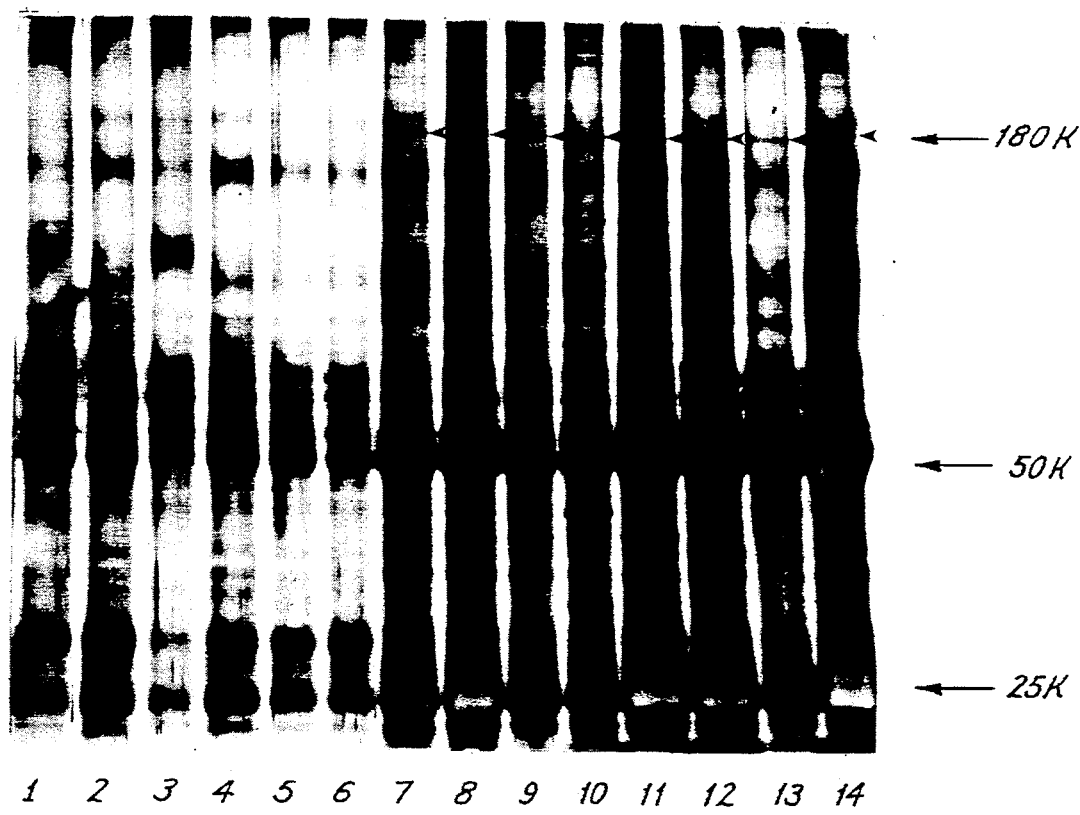
FIG. 2 shows SDS-PAGE protein profiles of urine samples obtained from bladder cancer patients (tracks 7 to 14) and age-matched controls (tracks 1 to 6) previously adsorbed by protein A-sepharose.

The present study further focused on comparing immunoglobulins and immunoglobulin-associated proteins in urine samples collected from controls and bladder cancer patients. A method previously described by Ey et al.[17] was adapted, with modification, for identifying and quantifying immunoglobulins and immune complexes (see above). Urine specimens that had undergone prior protein A-SEPHAROSE bead adsorption were eluted and subjected to SDS-PAGE Analyses. FIG. 2 shows that urine samples obtained from controls (tracks 1 to 6) and bladder cancer patients (tracks 7 to 14) differed in their overall silver-staining protein band intensity, a result similar to that observed in total protein profiles (see FIG. 1).

There were also numerous qualitative differences in the protein profiles between controls and bladder cancer patients and among different bladder cancer patients. In comparing these gel tracks, the criterion was to find a common protein(s) shared by all bladder cancer patients but absent from controls. Bladder cancer patients were found to share a 180-kDa marker protein (see arrow in FIG. 2) that was absent from control subjects. Because the general protein staining intensity of the control subjects in the SDS-PAGE gel was always less than that of the bladder cancer patients, the urine samples from 10 control subjects were re-examined by grossly overloading the SDS-PAGE gel with 3-fold more proteins; despite the overloading, none of the controls displayed this 180-kDa marker protein.

A large number of urine samples were collected from patients with various forms of bladder cancer, screened, and compared with the results with samples from control subjects. Of specimens from 101 bladder cancer patients tested, the presence of a unique 180-kDa marker protein was identified in the urine of 72 (71.3 percent, Table 1). Samples from none of the 37 control subjects contained this urinary marker protein. Histologically, transitional cell carcinoma was the single dominant form of cancer investigated (92 percent of the cases). Because of the smaller number of other bladder cancer cases studied, it was not possible to definitively identify differences in the appearance of the 180-kDa marker protein that may exist among other forms of bladder cancers (see Table 1).

TABLE 1

Presence of a 180-kDa marker protein in urine collected from patients with various types of bladder cancer

| Type of Bladder Cancer | Patients | | 180-kDa Marker Protein | | | |
|---|---|---|---|---|---|---|
| | | | Positive | | Negative | |
| | No. | (%) | No. | (%) | No. | (%) |
| Transitional cell carcinoma | 93 | (92) | 69 | (74.2) | 24 | (25.8) |
| Squamous cell carcinoma | 4 | (4) | 2 | (50) | 2 | (50) |
| Adenocarcinoma | 1 | (1) | 0 | (0) | 1 | (100) |
| Sarcoma | 2 | (2) | 1 | (50) | 1 | (50) |
| Small cell carcinoma | 1 | (1) | 0 | (0) | 1 | (100) |
| Total | 101 | (100) | 72 | (71.3) | 29 | (28.7) |

This 180-kDa marker protein appears to be bladder cancer-specific because it was not detected in urine samples collected from 35 patients with other neoplasms (Table 2).

TABLE 2

The absence of a 180-kDa marker protein in urine specimens collected from patients with other neoplasms

| Neoplasm | No. Patients | 180 kDa Marker Protein | |
|---|---|---|---|
| | | Positive | Negative |
| Other Cancers | | | |
| Prostate | 7 | 0 | 7 |
| Colon | 3 | 0 | 3 |
| Cervix | 5 | 0 | 5 |
| Ovary | 3 | 0 | 1 |
| Vagina | 1 | 0 | 1 |
| Liver | 1 | 0 | 1 |
| Lung | 8 | 0 | 8 |
| Esophagus | 2 | 0 | 2 |
| Pancreas | 3 | 0 | 3 |
| BPH* | 2 | 0 | 2 |
| Total | 35 | 0 | 35 |

*BPH - benign prostatic hyperplasia

Patients with bladder cancer were further analyzed according to gender and the presence of a bladder infection at the time of urine collection. Table 3 shows that 83.2 percent of the patients from whom urine specimens were collected were men, 69 percent of whom had a detectable 180-kDa marker protein. Of the women (16.8%) with bladder cancer, the marker protein was detected in the urine of 82.4 percent.

TABLE 3

Presence of a 180-kDa marker protein in urine according to patients' gender

| Gender | Patients | | 180kDa Marker Protein | | | |
|---|---|---|---|---|---|---|
| | | | Positive | | Negative | |
| | No. | (%) | No. | (%) | No. | (%) |
| Male | 84 | (83.2) | 58 | (69.0) | 26 | (31.0) |
| Female | 17 | (16.8) | 14 | (82.4) | 3 | (17.6) |
| Total | 101 | (100) | 72 | (71.3) | 29 | (28.7) |

As evaluated by bacterial culture, 23.3 percent (7/30) of the patients had a urinary bladder infection at the time of urine collection (Table 4).

TABLE 4

Presence of a 180-kDa marker protein in urine specimens collected from patients with or without evidence of bladder infection

| Infection Status | Patients | | 180kDa Marker Protein | | | |
|---|---|---|---|---|---|---|
| | | | Positive | | Negative | |
| | No. | (%) | No. | (%) | No. | (%) |
| Bladder infection | 7 | (23.3) | 5 | (71.4) | 2 | (28.6) |
| Men | 5 | | 4 | (80) | 1 | (20) |
| Women | 2 | | 1 | (50) | 1 | (50) |
| No bladder infection | 23 | (76.7) | 17 | (73.9) | 6 | (26.1) |
| Men | 20 | | 14 | (70) | 6 | (30) |
| Women | 3 | | 3 | (100) | 0 | (0) |
| Total | 30 | (100) | 22 | (73.3) | 8 | (26.7) |

There appeared to be no significant difference in the detection of the 180-kDa marker protein between patients with or without documented evidence of urinary bladder infection (71.4% vs 73.9%, respectively). Furthermore, comparison between men and women with respect to urinary tract infection status revealed compelling evidence that the presence of a 180-kDa marker protein in the urine was not related to bladder infection at the time urine samples were collected. This marker was identified in 80 percent versus 70 percent of men in infected and noninfected groups as compared with 50 percent versus 100 percent of women in infected and noninfected groups, respectively.

Figure 3:
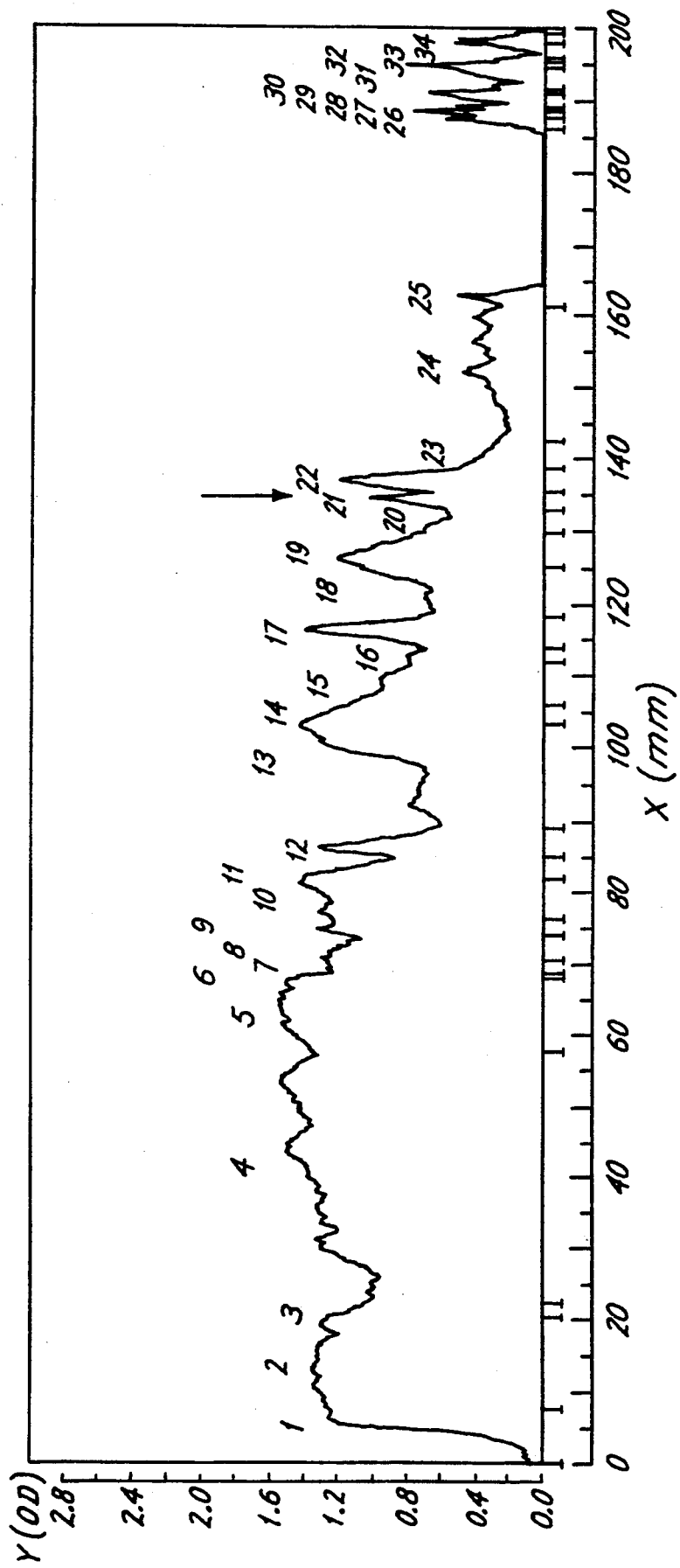
FIG. 3 shows densitometer scanning of a representative urine sample obtained from a bladder cancer patient. The area under the curve was calculated by point-to-point baseline substraction according to the standarized BioRad densitometer software system.

This 180-kDa marker protein represented a total of about 1.5 percent to 3.2 percent of the protein A-SEPHAROSE-bound protein as analyzed by SDS-PAGE, with proteins stained by silver reagents and scanned by a densitometer (FIG. 3).

Figure 4:
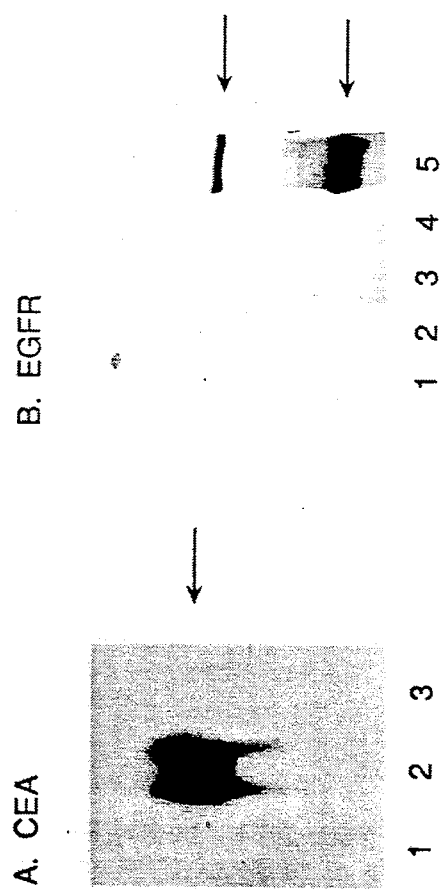
FIG. 4 shows A) Wester blot or urine (track 1) and serum (track 3) samples obtained from a bladder cancer patient as compared with carcinoembryonic antigen (CEA) (track 2). The arrow indicated the location of CEA at a MW of 200 kDa and B) Western blot of epidermal growth factor receptor (EGFR) obtained from A431 cells (track 5 ) and from urine samples of normal controls (tracks 1 and 2) and bladder cancer patients (tracks 3 and 4). The arrows indicated the EGFR (top, 175 kDa), and its intermediate precursor (bottom, 95 kDa).[21]
Figure 5:
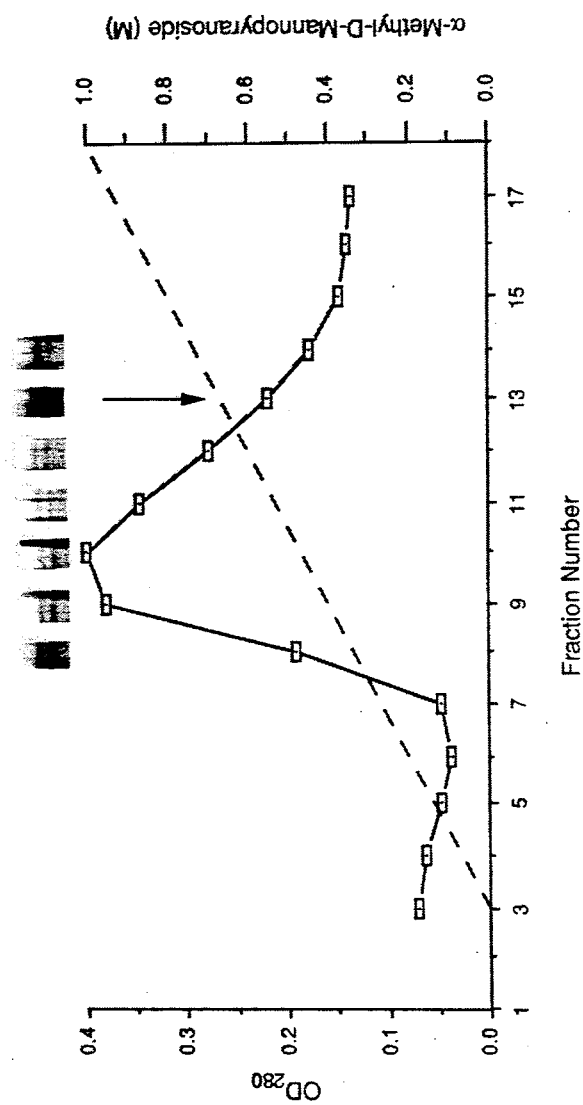
FIG. 5 shows concanavalin A-SEPHAROSE column chromatography or urine proteins isolated from a patient with bladder cancer.

To further positively identify the biochemical nature of the 180-kDa marker protein, two approaches were followed. First, the 180-kDa marker protein was compared to CEA and EGFR, both of which are known to contain a single polypeptide and have a MW of about 180 kDa. Second, the 180-kDa protein was tested as a glycoprotein, which can be adsorbed by lectin-conjugated SEPHAROSE beads. FIG. 4A shows that CEA-antibody-reactive material was absent from one representative urine specimen (track 1) and serum specimen (track 3) from a bladder cancer patient who had been diagnosed as positive for the subject 180-kDa marker protein. Track 2 indicates that, in contrast, purified CEA, loaded onto the gel with a silver-stain intensity closely approximating that of the 180-kDa marker protein, reacted strongly with a $[^{125}I]$-labeled monoclonal antibody directed against CEA. Using the western blot procedure to detect the EGFR, it was found that A-431 cells, a human epidermal cell line that is known to contain a high level of EGFR, exhibited a high level of immunoreactive EGFR. None of the EGFR- antibody-reactive material could be detected in the urine samples of either controls (FIG. 4B, tracks 1 and 2) or bladder cancer patients (FIG. 4B, tracks 3 and 4). The 180-kDa marker protein of the present invention appears to be associated tightly with the concanavalin A-conjugated SEPHAROSE beads and could be eluted by alpha-methyl-D-mannopyranoside, preferentially at 0.72M (FIG. 5).

Figure 6:
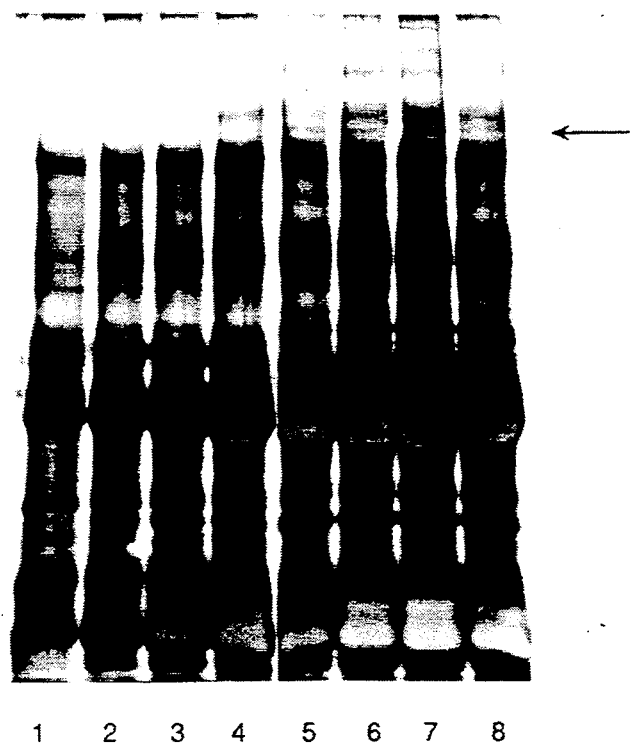
FIG. 6 shows adsorption of 180-kDa protein by protein A-SEPHAROSE in the presence of increasing amounts of exogenously added purified human IgG (0-50 ug). Urine samples derived from normal controls (tracks 1 to 4) and bladder cancer patients (tracks 5 to 8) were pre-incubated with various amounts of purified human IgG (tracks 1 and 5, 0 ug; tracks 2 and 6, 10 ug; tracks 3 and 7, 25 ug; tracks 4 and 8, 50 ug) at 4'C for 1.5 hr prior to protein A-SEPHAROSE adsorption and SDS-PAGE analysis.

Whether the 180-kDa protein was present as a free form in control subjects but potentially bound to varying degrees to human immunoglobulin G (IgG) as an immune complex in the urine of bladder cancer patients was investigated. Various amounts (up to 50 ug) of human IgG were added to the urine samples from both normal controls (FIG. 6, tracks 1 to 4) and bladder cancer patients (tracks 5 to 8) prior to protein A-SEPHAROSE adsorption. The purpose of adding exogenous IgG was to convert any free 180-kDa marker protein to a bound form, which then could be adsorbed by protein A. Results indicated that adding exogenous human IgG did not enrich the levels of the 180-kDa protein detected by the method of this invention.

The above studies identified a new urine-derived 180-kDa protein marker specific to bladder tumors. This 180-kDa protein accounted for 1.5 percent to 3.2 percent of the total protein A-SEPHAROSE-adsorbed urine protein as determined by densitometer tracing. Although this protein could be concentrated and somewhat purified by the use of protein A covalently linked to SEPHAROSE beads, its concentration was not further increased by adding exogenous human IgG to urine samples. Most of the 180-kDa protein was already associated with IgG as an apparent antigen-antibody complex. Alternatively, however, the 180-kDa protein could conceivably be bound nonspecifically to protein A-SEPHAROSE. O'Brien et al.[6] detected IgG in the void volume of a Sephadex G-200 column of urine specimens from bladder cancer patients. They suggested that IgG may be bound to some other urinary component as an antigen-antibody immune complex. Babaian et al[18] showed that the content of immune complexes increased in the urine samples collected from patients with bladder cancer. Kobayashi et al.[19] demonstrated a positive correlation between the level of immune complex in sera of bladder cancer patients and the extent of bladder tumor invasion and the degree of malignancy. None of the previous studies, however, has identified the possible presence of a common antigen associated with immune complex that may be bladder cancer specific.

The present invention also involves the observation that a 180-kDa band appeared in serum samples collected from both normal subjects and bladder cancer patients. Whether this serum protein and the urinary marker protein are identical remains to be yet established. However, the bladder cancer-specific 180 kDa urine protein is unlikely to be the result of blood contamination for the following reasons: 1. Gross hematuria does not correlate with the presence of the 180-kDa marker protein. This data indicated that samples from 13.2 percent (10/76) of 180-kDa positive and 16.1 percent (5/31) of 180-kDa negative patients showed gross hematuria. 2. There was no consistent correlation between the intensity of silver-staining bands in the regions of heavy and light chains of immunoglobulin and that of the 180-kDa marker protein in urine samples. 3. The concanavalin-A column chromatographic elution profile of the blood protein is vastly different from that of this marker protein from urine specimens. 4. Sequential urine samples collected directly from an ileal conduit still contained the 180-kDa marker protein.

The latter observation raised the question of the origin of the 180-kDa marker protein. Two theories could possibly identify the source of this marker protein. The first theory assumes that the 180-kDa protein is derived directly from bladder cancer tissues, has a special affinity for immunoglobulin molecules and exists in the urine as an antigen-antibody complex. The second theory assumes that the 180-kDa protein is a blood component which appears in the urine through glomerular filtration and/or tubular secretion. With regard to the first possibility, preliminary evidence has been obtained to indicate that a protein with an apparent MW of 180 kDa was actually present in a human bladder epithelial cancer cell line. This marker protein can be metabolically labeled with [$^{35}$S]-methionine and immunoadsorbed by protein A-SEPHAROSE. It is conceivable that this bladder tumor-specific antigen-antibody complex may be deposited on the surface of the bladder cancer cells. The appearance of this protein in the urine of postcystectomy bladder cancer patients may be attributable to residual bladder cancer in the upper urinary tract. With regard to the second possibility, it is known that bladder cancer-derived antigen-antibody complexes may be deposited onto glomeruli and cause a nephrotic lesion. This lesion might result in leakage of the antigen-antibody complex into the urine.[20] Therefore, the 180-kDa marker protein might represent a bladder-specific antigen that is associated with urinary immune complexes. It is understood that the above hypotheses are meant to elucidate the invention even more clearly and not to limit this invention because such hypotheses may be inaccurate or incomplete.

EXAMPLE 2

The urine of 93 patients who underwent a radical cystectomy for transitional cell carcinoma of the bladder between October 1986 and May 1988 at The University of Texas M. D. Anderson Cancer Center was examined preoperatively for the presence of a common tumor-associated protein. The median age of our patients was 65 years (range, 27–82 years). Pathologic assessment of the cystectomy specimen revealed that 27 patients had superficial disease (8 CIS, 10 stage 0, and 9 stage A), 43 patients had infiltrating disease (21 stage B and 22 stage C), and 23 had metastatic disease (21 stage $D_1$ and 2 stage $D_2$) Tumors were grade 2 in 21 patients and grade 3 in 64. The neoplasm was not graded in 8 patients with carcinoma in situ (CIS).

Most urine samples were catheterized specimens obtained in the operating room immediately before cystectomy. The samples, ranging in volume from 80 to 100 ml, were immediately transported on ice for analysis. Clean-catch voided urine specimens were collected from 37 normal controls (24 age 24–46 years and 13 age 57–78 years) and from 35 patients with non-bladder neoplasms (benign prostatic hyperplasia and primary cancers of the prostate, colon, cervix, vagina, ovary, liver, lung, esophagus, and pancreas). All the samples were then handled in an identical manner and processed as described in Example 1.

Statistical analysis was performed by the Fischer exact test and by the method of binomial distribution.[25,26]

The results from these studies were as follows. Overall, urine samples from 74.2 percent (69/93) of the patients with transitional cell carcinoma of the bladder were positive for a 180-kDa protein. The marker incidence by stage and grade is depicted in Table 5.

TABLE 5

Pathologic features of the bladder lesion and prostate in the surveyed patients

| | Patient Category | |
|---|---|---|
| Feature | Marker-Negative n = 24 | Marker-Positive n = 69 |
| Tumors graded | 22 | 63 |
| Grade 1 | 0 | 0 |
| Grade 2 | 7 (31.8%) | 14 (22.2%) |
| Grade 3 | 15 | 49 |
| Transition form | | |
| No | 20 | 56 |
| Yes | 4 (16.7%) | 13 (18.8%) |
| Concomitant adenocarcinoma of the prostate | | |
| Yes | 11 (45.8%) | 24 (34.8%) |
| Stage | | |
| Ax | 7 | 12 |
| A | 4 | 9 |
| B | — | 2 |
| C | — | 1 |
| D | — | — |
| No | 13 | 44 |
| Transitional cell carcinoma of the prostate | | |
| No | 21 | 53 |
| Yes | 3 (12.5%) | 16 (23.2%) |
| Urethra | — | 9 |
| Duct | 3 | 13 |
| Stroma | 1 | 3 |
| Lymphatic permeation | | |
| Yes | 10 (41.7%) | 30 (43.5%) |
| No | 14 | 37 |

None of the controls, neither the normal persons nor those with a neoplasm other than transitional cell carcinoma, was found to have a 180-kDa urinary protein (as described in Example 1). The patients whose urine was negative for the 180-kDa urinary protein were compared with those whose urine was positive according to various pathologic and clinical features (Tables 5-7).

TABLE 6

Clinical features of the 93 patients with TCC whose urine was examined for a urinary protein marker

| Feature | Marker-Negative n = 24 | Marker-Positive n = 69 |
|---|---|---|
| Age range | 47-75 | 27-82 |
| Sex | | |
| Male | 23 | 56 |
| Female | 1 (4.2%) | 13 (18.8%) |
| Prior systemic chemotherapy | | |
| No | 17 | 64 |
| Yes | 7 (29.2%) | 5 (7.2%) |
| Intravesicle chemotherapy | | |
| No | 20 | 65 |
| Yes | 4 (16.7%) | 4 (5.8%) |
| Prior irradiation | | |
| No | 22 | 65 |
| Yes | 2 (8.3%) | 4 (5.8%) |

TABLE 7

Relationship of stage to the 180-kDa urinary protein

| | Marker-Negative n = 24 | | Marker-Positive n = 69 | | % of Total |
|---|---|---|---|---|---|
| Feature | No. | (%) | No. | (%) | n = 93 |
| Clinical stage | | | | | |
| CIS | 2 | (8.3) | 4 | (5.8) | 6.5 |
| O | 3 | (12.5) | 7 | (10.1) | 10.8 |
| A | 6 | (25.0) | 7 | (10.1) | 14 |
| B | 7 | (29.2) | 36 | (52.2) | 46.2 |
| C | 6 | (25.0) | 10 | (14.5) | 17.2 |
| $D_1$ | — | | 3 | (4.3) | 3.2 |
| $D_2$ | — | | 1 | (1.4) | 1.1 |
| Missing | — | | 1 | (1.4) | 1.1 |
| Pathologic stage | | | | | |
| CIS | 2 | (8.3) | 6 | (8.7) | 8.6 |
| O | 5 | (20.8) | 5 | (7.2) | 10.8 |
| A | 4 | (16.7) | 5 | (7.2) | 9.7 |
| B | 5 | (20.8) | 16 | (23.2) | 22.6 |
| C | 3 | (12.5) | 19 | (27.5) | 23.7 |
| $D_1$ | 5 | (20.8) | 16 | (23.2) | 22.6 |
| $D_2$ | — | | 2 | (2.9) | 2.2 |
| Stage of tumor in bladder | | | | | |
| CIS | 2 | (8.3) | 7 | (10.1) | 9.7 |
| O | 5 | (20.8) | 5 | (7.2) | 10.8 |
| A | 4 | (16.7) | 5 | (7.2) | 9.7 |
| B | 6 | (25.0) | 23 | (33.3) | 31.2 |
| C | 7 | (29.2) | 29 | (42) | 38.7 |

There were no significant differences in the distribution of marker-negative or marker-positive patients with respect to tumor grade, clinical or pathologic stage, presence of histologic variants of transitional cell carcinoma, concomitant prostate cancer as detected by whole-mount step-sectioning, presence of synchronous transitional cell carcinoma of the prostate, lymphatic permeation, age, gender, history of intravesical chemotherapy, or prior radiation therapy. The pathologic stage of the tumor in the bladder at the time of cystectomy was also not significantly different between the protein marker-positive and marker-negative patients.

A significantly greater percentage of protein-negative patients (29.2 percent) than of marker-positive patients (7.2 percent) had received prior chemotherapy. However, the therapeutic drug history of the protein-negative patients was noncontributory towards explaining the differences in the detection of the 180-kDa urinary marker protein.

The occurrence of proteinuria in cancer patients is well known, as is the presence of urinary immunoglobulins.[2] However, neither the source of the proteins nor their significance has been elucidated. Nonspecific proteins that have been identified in the urine of bladder cancer patients include alpha-2-macroglobulin, haptoglobin, fibrinogen and fibrin-degradation products, IgA, IgM, IgG, transferin, albumin, and orosomucoid. The potential relationships of either the presence or the quantity of urinary immune complexes and immunoglobulins to the stage and size of bladder cancer has been previously reported.[18,27] The present investigations have led to the identification of a urinary marker protein of 180-kDa that appears to be bladder cancer-specific. This marker is found in 0–9.5 percent of normal controls and in 0–10 percent of patients with malignant neoplasms other than transitional cell carcinoma at the 95 percent confidence limit.

It appears that the incidence of this 180-kDa marker is directly related to the pathologic stage of disease (Table 8).

TABLE 8

Relationship of 180-kDa protein to pathologic stage

| Stage | No. Patients | Marker-Negative No. | (%) | Marker-Positive No. | (%) |
|---|---|---|---|---|---|
| CIS | 8 | 2 | (25) | 6 | (75) |
| O | 10 | 5 | (50) | 5 | (50) |
| A | 9 | 4 | (44.4) | 5 | (55.6) |
| B | 21 | 5 | (23.8) | 16 | (76.2) |
| C | 22 | 3 | (13.6) | 19 | (86.4) |
| $D_1$ | 21 | 5 | (23.8) | 16 | (76.4) |
| $D_2$ | 2 | 0 |  | 2 | (100) |
| Total | 93 | 24 |  | 69 |  |

However, patients who have CIS have a higher incidence of a positive marker than patients with other superficial stages of disease, albeit the difference not being of statistical significance. Interestingly, the incidence of the 180-kDa protein is higher in patients with stage C disease than in those with stage $D_1$. At the time of cystectomy, in the $D_1$ patients the tumor in the bladder extended perivesically in 13 and into muscle only in 8 patients. Chemotherapy did not seem to influence this finding, since only 3 of the 21 patients (1 marker-positive, 2 marker-negative) had received systemic chemotherapy before undergoing cystectomy.

Overall, a statistically significant higher incidence of marker-negative patients had undergone neoadjuvant chemotherapy (P=0.018). Furthermore, 50 percent of marker-negative patients had received either chemotherapy (7 systemic, 4 intravesical) or radiation therapy (2) prior to cystectomy and urine collection, as compared with 17.4 percent of the marker-positive patients. Whether or not these therapies before sample collection affected the detectability or synthesis of the 180-kDa protein marker is undetermined at this time.

Two pathologic features not examined that could possibly help to explain the detectability of this marker are actual tumor size and tumor configuration, i.e., papillary or sessile. There appears to be no relationship between the presence and detection of this marker and urinary tract infection status. The specificity of this 180-kDa urinary protein marker appears to be high and, therefore, it should prove useful in diagnosing and staging bladder cancer.

EXAMPLE 3

Polyclonal antibodies have been raised which are specific for the 180 kDa marker protein described in Example 1. In this case, the 180 kDa protein was purified as described in Example 1 through the SDS-PAGE. After staining with Coomassie Blue the 180 kDa band was cut and homogenized with RIBI adjuvant. An adult New Zealand white female adult rabbit was injected subcutaneously with 300 micrograms of the 180 kDa protein at multiple sites along both sides of the spinal cord twice at a 20-day interval. After an additional 20 days a final multiple site injection of 80 micrograms protein in adjuvant was administered. During the seventh to ninth day after this final injection, the rabbit serum was tested for antibody titers. SDS-PAGE gels prepared from patient and control urinary protein samples as described in Example 1 were obtained. Materials of the electrophoresed gels were transferred onto nitrocellulose paper. The nitrocellulose paper was subsequently incubated with protein from the rabbit serum samples. After removal of unbound materials, the paper was treated with a secondary antibody which was goat anti-rabbit IgG conjugated to peroxydase. After washing unbound materials from the nitrocellulose paper, peroxydase substrate was added and color developed in a conventional manner. It was determined that specific rabbit IgG was present at the 180 kDa site.

Figures 7A, 7B:
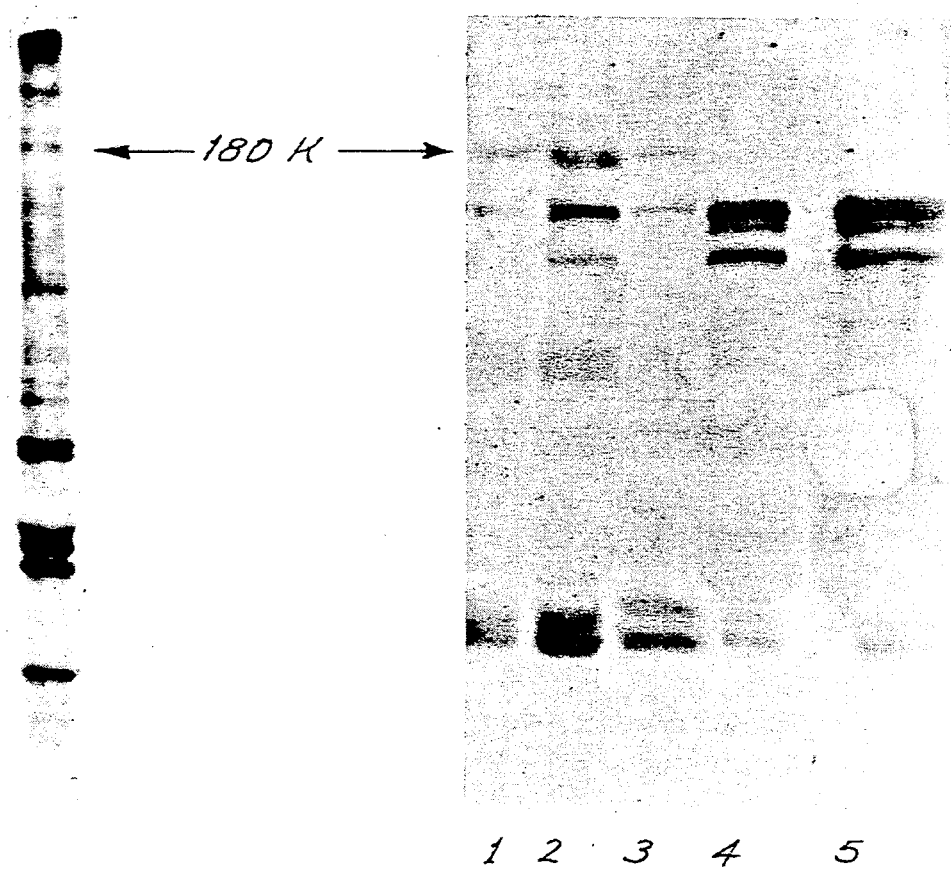
FIG. 7a shows a protein profile of [$^{35}$S]-methionine-labeled human bladder WH epithelial cells. The cells were prelabeled with [$^{356}$S]-methionine for 12 hours, and the cytosolic fraction was collected. Approximately 40,000 cpm-labeled material recovered from protein A-adsorption was loaded onto each track of the gel which was subjected to electrophoresis under similar conditions as that described in FIG. 2. The arrow indicates the presence of the 180-kDa protein associated with WH cell cytosol. A similar fraction associated with the cell culture medium and particulate fraction were not examined.
FIG. 7b shows a western blot of urine specimens obtained from bladder cancer patients (tracks 1, 2 and 3) and controls (tracks 4 and 5) on nitrocellulose paper reacted with polyclonal antibody prepared in the rabit against PAGE-purified 180 kDa protein. One mg of total urine protein was used as the starting material which was subjected to protein A-SEPHAROSE treatment as described in FIG. 2. Note that the antibody reacted with multiple bands in both control and patient samples. However, the antibody recognizes a specific 180 kDa band (see arrow) only in the patient samples.

FIG. 7a shows a protein profile of [35S]-methionine-labeled human bladder WH epithelial cells. The cells were prelabeled with [35S]-methionine for 12 hours, and the cytosolic fraction was collected. Approximately 40,000 cpm-labeled material recovered from protein A-adsorption was loaded onto each track of the gel which was subjected to electrophoresis under similar conditions as that described in FIG. 2. The arrow indicates the presence of the 180-kDa protein associated with WH cell cytosol. A similar fraction associated with the cell culture medium and particulate fraction were not examined. FIG. 7b shows the Western blot of urine specimens obtained from bladder cancer patients (tracks 1, 2 and 3) and controls (tracks 4 and 5) on the nitrocellulose paper reacted with the polyclonal antibody prepared in the rabbit against a PAGE-purified 180 kDa protein. One mg of total urine protein was utilized initially as the starting material subjected to a protein A-SEPHAROSE treatment as described in Example 1. As seen in FIG. 7b, the antibody had reacted with multiple bands in both the control and patient samples. Particular significance, however, is that there was a specific 180 kDa band specified only in the patient samples (see arrow in FIG. 7b ). This procedure is currently being further refined by removal of nonspecific reactivity according to previously described procedures (Cho[Zhau]and Chung, 1982)[28].

EXAMPLE 4

This prophetic example describes methods to be used in the development of polyclonal and monoclonal antibodies specifically binding the 180 kDa bladder cancer specific antigen described earlier herein. Such antibodies may be used for the ready detection of this bladder cancer-specific proteinaceous marker. The methodology described below is designed to produce both monoclonal and polyclonal antibodies that recognize antigenic determinants of the 180-kDa protein. Once the 180 kDa protein-specific antibodies are available, many other biochemical studies will then become feasible. Such studies will include purification of the 180-kDa protein by antibody-affinity column chromatography; biochemical characterization of this protein; and use of the specific antibody to detect and quantitate the levels of 180-kDa protein in various clinical conditions, such as in patients with low-grade and early stages of bladder tumors and patients who have and have not undergone chemotherapy and radiation therapy.

Both monoclonal and polyclonal antibodies against the 180-kDa protein are described for the reasons that the monoclonal antibody may be produced in low titer, and the clones that produce the monoclonal antibodies may be unstable and have a finite life span. Similarly, the polyclonal antibody may be less specific and may cross-react with other urine proteins. Producing both antibodies will maximize the opportunity to select the best possible reagents so that other biochemical studies and clinical investigations can be performed successfully. Such specific antibodies should allow detection of the diagnostic 180 kDa antigen without extensive prior treatment.

Techniques to be used for the production of monoclonal antibody (MoAb) are described below:

180-kDa protein used for immunization: As described in earlier Examples, urine protein from bladder cancer patient will be adsorbed with protein A-SEPHAROSE beads and then subjected to 7.5% SDS-PAGE analysis. The silver-stained or Coomassie Blue-stained 180-kDa protein band will be cut, homogenized, and mixed with RIBI adjuvant system (RIBI, 1985) for injection (as described in Example 3). The RIBI adjuvant system contains only 2% oil, thereby reducing emulsion viscosity. This adjuvant system is not only easier to handle than commoner adjuvants but is also more immunogenic and causes less irritation to the experimental animal. Advantages of using proteins in polyacrylamide gels for immunization are the antigen associated with the large polyacrylamide particles are more immunogenic and that the protein trapped in the acrylamide matrix is not rapidly degraded; the animal is therefore exposed to the immunogen for a longer duration.[29] It is anticipated that the antibodies developed by this method should recognize epitopes of the 180-kDa antigen and bind avidly to denatured proteins on Western blot.

Mouse myeloma cell line used for hybridization: Azaguanine-resistant mouse myeloma SP2/0 non-producer cell line obtained from the American Tissue Culture Collection, Rockville, Maryland, will be maintained. The SP2/0 cell line has been selected for 8-azaguanine resistance and does not survive in medium containing hypoxanthine, aminopterin, and thymidine (HAT). Cells will be propagated in Iscove's modified Dulbecco's medium supplemented with 10% fetal bovine serum.

Method of immunization: Each of four female balb/c mice of approximately 2 months of age will be immunized intraperitoneally with 50 ug of 180-kDa protein antigens homogenized with RIBI adjuvant (day 0). The mice will then be given three consecutive intraperitoneal injections of the 180-kDa protein antigens mixed with RIBI adjuvant (days 10, 20, and 30). Approximately one month after the fourth injection, the mice will be given a booster inoculation of 25 ug 180-kDa protein. Three days after the booster injection, a small amount of blood will be drawn from the tail vein of the immunized mice and tested for the presence of circulating antibodies to the 180-kDa antigen. An immunized mouse producing a reasonable titer of circulating antibody to the 180-kDa protein will be killed and its spleen aseptically removed for cell fusion.

Cell fusion: The basic method of somatic cell fusion of Kohler and Milstein (1975)[30] will be used with some modification as described previously by Chan et al. (1986)[31]. Immune splenocytes (10 cells) obtained from one hyperimmunized mouse will be used to fuse with 8-azaguanine-resistant SP2/0 mouse myeloma cells ($10^7$ cells), suing 37% (v/v) polyethylene glycol 1,500 (MW 500–600, M.A. Bioproducts, Inc.) as the cell-fusing reagent.

Selection of hybridomas and cloninq procedure: Fused cells will be maintained for two days in growth medium that has been conditioned with SP2/0 cells and then plated in five 96-well microtiter plates in growth medium containing HAT (selection medium). At the end of two weeks cells will be screened for antibody production by indirect enzyme-linked imunosorbant assay (ELISA) as described later herein.

For the initial screening, urinary proteins equivalent to 2.5 ug from either normal controls or bladder cancer patients will be immobilized onto the bottoms of the 96-well microtiter plates by incubating at 4° C. overnight. The culture medium from the wells propagating the splenocyte-myeloma (hybrid) cells growing in the selection medium will be assayed for antibodies that react with the immobilized antigens. The isolation of hybridoma clones producing monoclonal antibodies against the 180-kDa protein is anticipated. The positive hybridoma cultures will be single-cell-cloned by limiting dilutions in SP2/0-conditioned Iscove's modified Dulbecco's medium supplemented with 20% fetal bovine serum. Monoclonal antibody will be produced either as a cultured hybridoma or as ascites in an athymic nude mouse (Chan et al., 1986; Chan, 1983)[31, 32].

Determination of antibody isotypes: The isotypes of the immunoglobulin(s) produced by cloned hybridoma cell clones will be determined by ELISA, employing a commercial isotyping kit purchased from Kirkegaard and Perry Laboratory.

Production of polyclonal antibodies in rabbits: Three adult New Zealand white female rabbits will be immunized with the urinary 180-kDa marker protein purified by SDS-PAGE according to the procedure described in Example 1. Rabbits will be immunized at multiple sites intradermally and subcutaneously along both sides of the spinal cord (see Example 3). About 0.1 to 0.2 ml will be injected per site for a total of 2.5 to 3.0 ml (300 ug of 180-kDa protein will be mixed with 2.0 ml of RIBI adjuvant). The injections will be given at 2- to 4-week intervals for a total of three to four injections. Seven to nine days after the last immunization with 80 ug 180-kDa protein, rabbit sera will be obtained to test the titer of the antibody by an ELISA procedure. In addition, the specificity of the polyclonal antibody against the 180-kDa marker protein will be evaluated by a Western blot procedure (Towbin et al., 1979) comparing the reactivity of this antibody to urine proteins from normal controls and bladder cancer patients. One milligram of urine protein will be treated with 2.5 mg protein A-SEPHAROSE beads, washed, and eluted by a batch procedure (see Appendix 2). The protein A-bound materials will be analyzed by SDS-PAGE, and transferred electro-phoretically to nitrocellulose paper and blotted with a 180-kDa-specific antibody. The location of the urinary 180-kDa protein will be visualized by a color reaction after the immunoblot has been treated with a secondary antibody conjugating with an enzyme such as alkaline phosphatase and the substrate according, for example, to the procedures described by Hsu (1981)[33]. The specificity of this antibody can be tested by prior immunoprecipitation of the antibody with the purified 180-kDa marker protein.

Preliminary experiments as in Example 3 describe raising of polyclonal antibodies against 180-kDa marker protein. FIG. 7b showed that this polyclonal antibody indeed reacted with the 180-kDa marker protein (see arrow) in urine specimens collected from bladder cancer patients, but, in addition, also reacted with other urinary proteins in the specimens obtained from both control and bladder cancer patients. Employing appropriate immunoadsorption procedure to remove nonspecific reactivity in order to yield a 180-kDa marker protein-specific antibody according to previously described procedures will be employed (Chao [Zhau]and Chung, 1982)[28].

ELISA (enzyme-linked immunosorbant assay): Two and one half micrograms of urine proteins from both controls and patients will be coated on 96-well microtiter plates. The peroxidase- or alkaline phosphatase-conjugated antibody (goat anti-rabbit antibody for polyclonal and goat anti-mouse antibody for monoclonal) will be used as a secondary antibody. The detailed procedures described by Dunbar (1987)[29] will be followed. Controls for each assay will include: a) no antigen adsorbed to wells, b) no primary antibody, c) nonimmune serum, and, d) no secondary antibody. The intensity of antigen-antibody reactions will be determined by a microtiter ELISA reader.

RIA (Radioimmunoassay): The 180-kDa marker protein will be iodinated and the concentration of 180-kDa protein in urine samples will be determined by RIA. Standard curves of the 180-kDa marker protein will be established by using a protein concentration in the range of 0.1 to 10 ug/ml. The radioactive 180-kDa protein will be immunoprecipitated by 180-kDa-specific antibody and counted by a gamma-counter. The concentration of 180-kDa protein in unknown urine samples will be calculated from a standard curve which is established by plotting the log of bound (B, in the presence of competitor)/bound (Bo, in the absence of competitor) against the logarithm of competitor ligand concentration (Rodbard, 1971)[34].

Western blot: Unknown urine samples will be separated by SDS-PAGE and transblotted onto nitrocellulose paper according to the procedure of Towbin et al. (1979). The paper will be incubated with [$^{125}$I]-labelled antibody, and total radioactivity associated with the 180-kDa band should correlate quantitatively with the amount of 180-kDa protein present in the unknown samples. This can be confirmed by using known amount of 180-kDa protein as the antigen. If the specific bound labeled antibody to the nitrocellulose paper is limited to only the 180-kDa protein, an alternative dot blot procedure will be developed to quantitate this marker protein.

Statistical analyses: All results will be expressed as mean ±S.E. The Student t test and Wilcoxon rank sum test (Steel and Torrie, 1980)[35] will be performed to analyze the possible group differences between age-matched controls and patients with various stages or grades of bladder cancer. We will also compare the results in patients with bladder cancer before, during, and following therapy (immunotherapy, chemotherapy, and radiation therapy).

Anticipated Results and Potential Problems: It is expected that both monoclonal and polyclonal antibodies will be generated against the 180-kDa urinary marker protein. The monoclonal antibody may be more specific than the polyclonal antibody but may bind less avidly to the 180-kDa marker protein than the polyclonal antibody. To enhance the specificity of polyclonal antibody, immunoadsorption of this antibody preparation by whole urine proteins isolated from healthy control subjects will be performed. The residual unadsorbed antibody should react more specifically with 180-kDa marker protein.

Citations in the following list are incorporated by reference herein for the reasons cited.

REFERENCES

1. Silverberg, E. and Lubera, J.: Cancer statistics. Cancer, 38:14, 1988.
2. Johansson, B., Kistner, S. and Norberg, R.: Proteinuria in patients with urinary tract tumours. Scand. J. Urol. Nephrol., 5:229, 1971.
3. Hakala, T. R., Castro, A. E., Elliot, A. Y. and Fraley, E. E.: Humoral cytotoxicity in human transitional cell carcinoma. J. Urol., 111:382, 1974.
4. Troye, M., Perlmann, P., Pape, G. R., Spiegelberg, H. L., Naslund, I. and Gidlof, A.: The use of Fab fragments of anti-human immunoglobulin as analytic tools for establishing the involvement of immunoglobulin in the spontaneous cytotoxicity to cultured tumor cells by lymphocytes from patients with bladder carcinoma and from healthy donors. J. Immunol., 119:1061, 1977.
5. Gozzo, J., Gottschalk, R., O'Brien, P., Cronin, W. and Monaco, A. P.: Use of heterogeneous and monospecific antisera for the diagnosis of bladder cancer. J. Urol., 118:748, 1977.
6. O'Brien, P., Gozzo, J., Cronin, JW. and Monaco, A.: Qualitative analysis of proteinuria associated with bladder cancer. Invest. Urol., 17:28, 1979.
7. Wahren, B.: Tumor markers in gastrointestinal and urothelial cancers. Applied Methods in Oncology, 2:338, 1979.
8. Betkerur, V., Hlaing, V., Baumgartner, G., Rao, R., Rhee, H. and Guinan, P.: Screening tests for detection of bladder cancer. Urology, 16:16, 1980.
9. Betkerur, V., Baumgartner, G., Talluri, K., Shrifi, R., Nagubadi, S. and Guinan, P.: Urinary immunoglobulin A in the diagnosis of bladder cancer. J. Surg. Oncol., 16:215, 1981.
10. Huland, H., Otto, U. and Droese, M.: The value of urinary cytology, serum and urinary carcinoembryogenic antigen, rheumatoid factors, and urinary immunoglobulin concentration as tumor markers or prognostic factors in predicting progression of superficial bladder cancer. Eur. Urol.1, 9:346, 1983.
11. Zhau, H. Y. E. and Babaian, R. J.: Detection of immunoglobulin reactivity in urine specimens of bladder cancer patients (abstract). American Urological Association Annual Meeting, Boston, MA, 1988.
12. Langone, J. J.: Applications of immobilized protein A in immunochemical techniques. J. Immunol. Methods, 55:277, 1982.
13. Laemmli, U. K.: Cleavage of structural proteins during the assembly of the head of bacteriophage T4. Nature, 227:680, 1970.
14. Sammons, D. W., Adams, L. D. and Nishizawa, E. E.: Ultrasensitive silver-based color staining of polypeptides in polyacrylamide gels. Electrophoresis, 3:135, 1981.
15. Lowry, O. H., Rosenbrough, N. J., Farr, A. L. and Randall, R. J.: Protein measurement with the folin phenol reagent. J. Biol. Chem., 193:265, 1951.
16. Towbin, H. and Gordon, J.: Immunoblotting and dot immunobinding: current status and outlook. J. Immunol. Methods, 72:313, 1984.
17. Ey, P. L., Prowse, S. J. and Jenkin, C. F.: Isolation of pure IgG, IgG$_{2a}$ and IgG$_{2b}$ immunoglobulins from mouse serum using protein A-SEPHAROSE. Immunochemistry, 15:429, 1978.
18. Babaian, R. J., Watson, D. A. and Jones, J. M.: Immune complexes in urine and serum of patients with bladder cancer. J. Urol., 131:463, 1984.
19. Kobayashi, K., Umeda, T., Akaza, H., Niijima, T., Aikawa, T. and Tanimoto, K.: Circulating immune complexes in patients with bladder cancer and other malignancies of the urogenital tract. Urol. Int., 39:232, 1984.

20. Hemmingsen, L., Rasmussen, F., Skaarup, P. and Wolf, H.: Urinary protein profiles in patients with urothelial bladder tumors. Br. J. Urol., 53:324, 1981.

21. Mayes, E. LO. V. and Waterfield, M. D.,: Biosynthesis of the epidermal growth factor receptor in A431 cells. EMBO, 3:531, 1984.

22. Gozzo, J. J., Cronin, W. J., O'Brien, P. and Monaco, A. P.: Detection of tumor-associated antigens in urine from patients with bladder cancer. J. Urol., 124:804, 1980.

23. Rote, N. S., Gupta, R. K. and Morton, D. L.: Tumor-associated antigens detected by autologous sera in urine of patients with solid neoplasms. J. Surg. Res., 29:18, 1980.

24. Rife, C. C., Farrow, G. M. and Utz, D.C.: Urine cytology of transitional cell neoplasms. Urol. Clin. North Am., 6:599, 1979.

25. Matthews, D. E. and Farewell, V. T.: Using and Understanding Medical Statistics. Basel, New York: Karger, pp. 20–26, 1985.

26. Binominal distribution. In: Documenta. Geigy Scientific Table, 6th. Edited by K. Diem. New York: Geigy Pharmaceuticals, P. 85, 1962.

27. Johansson, B. and Kistner, S.: Proteinuria in patients with uroepithelial tumors with special regard to tumor size, clinical staging and grade of malignancy. Scand. J. Urol. Nephrol., 9:52, 1974.

28. Chao, H. E. [now Zhau]and Chung, L. W. K.: Neonatal Imprinting and Hepatic Cytochrome, p. 450, Molecular Pharmacology 21:744, 1982.

29. Dunbar, B. S. In: Two-dimensional electrophoresis and immunological techniques, p. 133, New York:-Plenum Press, 1987.

30. Kohler, G., and Milstein, C. Nature (Lond.) 256:495, 1975.

31. Chan, J. C., Keck, M. E., and Li, W. J. Biochem. Biophys. Res. Comm. 134:1223, 1986.

32. Chan, J. C. Monoclonal antibody News 2:7, 1983.

33. Hsu, S. M., Raine, L., and Fanger, H. Am. J. Clin. Pathol. 75:734, 1981.

34. Rodbard, D. In: Principles of Competitive Protein Binding Assays. Odell, W. D., and Daughaday, W. H. (eds), J. B. Lippincott Col, Phil., PA, p. 204, 1971.

35. Steel, R. G. D., and Torrie, J. H. In: Principles and procedures of statistics: a biochemical approach. New York:McGraw-Hill Book Co., p. 60, 1980.

Changes may be made in the elements described herein or in the steps or the sequence of steps of the method described herein without departing from the concept and scope of the invention as defined in the following claims.

What is claimed is:

1. A method for diagnosing bladder cancer, the method comprising:
    analysing a urine sample of a subject for a proteinaceous substance characterized as having a molecular weight of about 180 kDa, being in a complex with gamma globulin in the urine, being unreactive with antibodies specifically binding carcinoembryonic antigen or epidermal growth factor receptor, and is eluted at a concentration of about 0.72 M when bound to concanavalin A-Sepharose and subjected to a 0 to 1.0M α-methyl-D-mannopyranoside gradient;
    wherein said substance is present in a majority of bladder cancer victims.

2. The method of claim 1 wherein the detecting step involves adsorbing the complex on solid matrix-affixed Staphlocoocal protein A, forming an adsorbed complex.

3. The method of claim 2 wherein an eluent is applied to the adsorbed complex to product an eluate comprising the 180 kDa proteinaceous substance.

4. The method of claim 3 wherein the eluate is subjected to gel electrophoresis to separate proteinaceous components of the eluate concurrently with proteins having known molecular weights and acting as reference standards.

5. The method of claim 3 wherein the separated components are analyzed by Wester blot using an antibody specifically binding said proteinaceous substance.

6. A method for diagnosing bladder cancer in a subject, the method comprising:
    obtaining a urine sample from a subject;
    processing said sample to remove particular matter and low molecular weight dialysable substances, forming a processed sample;
    incubating said processed sample with solid matrix-affixed protein A, forming an adsorbed sample;
    separating said incubated solid matrix-affixed protein A, together with material adsorbed thereto, from remaining components of said adsorbed sample;
    treating said incubated solid matrix-affixed protein A having material adsorbed thereto with an eluent to form a proteinaceous eluate;
    separating proteinaceous components of said eluate according to their molecular weights by gel electrophoresis; and
    identifying a proteinaceous substance having a molecular weight of about 180 kDa present in said eluate, using concurrent gel electrophoresis of protein markers with known molecular weights as reference standards, wherein said substance is unreactive with antibodies specifically binding carcinoembryonic antigen or epidermal growth factor receptor and is eluted at a concentration of about 0.72M when bound to concanavalin A-Sepharose and subjected to a 0 to 1.0M α-methyl-D-mannopyranoside gradient;
    wherein the presence of said substance in a urine sample is found in a majority of bladder cancer victims.

7. A method for diagnosing bladder cancer in a subject, the method comprising:
    obtaining a urine sample from a subject;
    filtering said sample to remove particulate matter, forming a filtered sample;
    dialysing said filtered sample to remove low molecular weight soluble substances, forming a filtered, dialyzed sample;
    incubating said dialyzed, filtered sample with solid matrix-affixed protein A, forming a filtered, dialyzed, adsorbed sample;
    separating said filtered, dialysed, adsorbed sample from matrix-affixed protein A having material adsorbed thereto;
    treating said matrix-affixed protein A having material adsorbed thereto with an eluent to form a proteinaceous eluate;
    separating proteinaceous components of said eluate according to their molecular weights by gel electrophoresis; and
    assaying for a proteinaceous substance having a molecular weight of about 180 kDa by using a western blot involving application of antibody specific to said substance, wherein said substance is unreactive with antibodies specifically binding carcinoembryonic antigen or epidermal growth factor receptor and is eluted at a concentration of about 0.72 M when bound to concanavalin A-sepharose and subjected to a 0 to 1.0M α-methyl-D-mannopyranoside gradient;

wherein said substance is found in a majority of bladder cancer victims.

* * * * *

UNITED STATES PATENT AND TRADEMARK OFFICE
CERTIFICATE OF CORRECTION

PATENT NO. : 5,221,612  
DATED : June 22, 1993  
INVENTOR(S) : Zhau et al

Page 1 of 2

It is certified that error appears in the above-indentified patent and that said Letters Patent is hereby corrected as shown below:

In claim 1, line 55, column 19, delete the word "analysing" and substitute the word --analyzing--, therefor.

In claim 1, line 63, column 19, insert a space immediately after '1.0'.

In claim 2, line 1, column 20, delete the word "Staphlocoocal" and substitute the word --Staphlococcal--, therefor.

In claim 3, line 4, column 20, delete the word "product" and substitute the word --produce--, therefor.

In claim 5, line 12, column 20, delete the word "Wester" and substitute the word --Western--, therefor.

In claim 6, line 17, column 20, delete the word "particular" and substitute the word --particulate--, therefor.

In claim 6, line 18, column 20, delete the word "dialysable" and substitute the word --dialyzable--, therefor.

In claim 6, line 39, column 20, insert a space immediately after '0.72'.

In claim 6, line 40, column 20, insert a space immediately after '1.0'.

In claim 7, line 49, column 20, delete the word "dialysing" and substitute the word --dialyzing--, therefor.

In claim 7, line 55, column 20, delete the word "dialysed" and substitute the word --dialyzed--, therefor.

In claim 7, line 5, column 21, delete the word "sepharose" and substitute the word --Sepharose--, therefor.

UNITED STATES PATENT AND TRADEMARK OFFICE
CERTIFICATE OF CORRECTION

PATENT NO.　：　5,221,612
DATED　　　：　June 22, 1993
INVENTOR(S)：　Zhau et al

It is certified that error appears in the above-indentified patent and that said Letters Patent is hereby corrected as shown below:

In claim 7, line 1, column 22, insert a space immediately after '1.0'.

Signed and Sealed this

Eighteenth Day of January, 1994

*Attest:*

BRUCE LEHMAN

*Attesting Officer*　　　*Commissioner of Patents and Trademarks*